United States Patent [19]

Bowles

[11] Patent Number: 5,034,325

[45] Date of Patent: Jul. 23, 1991

[54] 5'-PHOSPHODIESTERASE ENZYME PREPARATION AND METHOD FOR ITS PRODUCTION

[75] Inventor: Linda K. Bowles, Chicago, Ill.

[73] Assignee: Enzyme Bio-Systems, Ltd., Englewood Cliffs, N.J.

[21] Appl. No.: 409,836

[22] Filed: Sep. 20, 1989

Related U.S. Application Data

[63] Continuation-in-part of Ser. No. 172,824, Mar. 25, 1988, abandoned.

[51] Int. Cl.$^5$ .......................... C12N 9/22; C12N 9/16
[52] U.S. Cl. .................... 435/199; 435/196; 435/188; 435/89
[58] Field of Search ............... 435/199, 196, 188, 89

[56] References Cited

U.S. PATENT DOCUMENTS

| | | | |
|---|---|---|---|
| 3,304,238 | 2/1967 | Laufer et al. | 195/52 |
| 3,459,637 | 8/1969 | Laufer et al. | 195/28 |
| 3,516,907 | 6/1970 | Kirchhoff et al. | 195/28 |
| 4,303,680 | 12/1981 | Tanekawa et al. | 426/60 |

OTHER PUBLICATIONS

Prentice, N. et al., (1984), J. Cereal Sci. 2, 153–164.
Kyong et al., Chem. Abst. 94:73083b (1981).
Prentice et al., Chem. Abst. 101:12581h (1984).

Primary Examiner—Elizabeth C. Weimar
Assistant Examiner—Charles L. Patterson
Attorney, Agent, or Firm—Rockey and Rifkin

[57] ABSTRACT

This invention relates to a 5'-phosphodiesterase enzyme preparation which exhibits excellent storage stability. It is obtained by a special extraction process from rapidly proliferating parts of the germinating seeds. The enzyme is useful for the hydrolysis of RNA to form 5'-nucleotides.

15 Claims, No Drawings

5'-PHOSPHODIESTERASE ENZYME PREPARATION AND METHOD FOR ITS PRODUCTION

This is a continuation-in-part of application Ser. No. 172,824, filed March 25, 1988.

FIELD OF THE INVENTION

The present invention relates to a storage-stable 5'-phosphodiesterase enzyme preparation and to a method for its commercial production by extraction of rapidly proliferating parts of germinating seeds.

BACKGROUND OF THE INVENTION

Ribonucleic acid (hereinafter RNA) is a complex polymer occurring in living organisms. Certain enzymes are capable of splitting the RNA molecule into smaller subunits known as nucleotides. The 5'-nucleotides are of particular interest because of their ability to improve the richness and intensity of flavors without themselves contributing to taste of a food product. For this reason, there is considerable commercial interest in the preparation of the enzyme which hydrolyzes RNA to form 5'-nucleotides. This enzyme is known as 5'-phosphodiesterase.

It is well known that rapidly proliferating parts of germinating seeds, such as the rootlets and stems, contain 5'-phosphodiesterase. However, these materials contain other enzymes which are extracted along with the 5'-phosphodiesterase. Some of these other enzymes in the crude extract cause further hydrolysis of 5'-nucleotides. This makes the crude extracts unsuitable for use in preparing 5'-nucleotides from RNA.

In U.S. Pat. No. 3,304,238, there is disclosed a method for preparing an aqueous enzyme medium capable of forming 5'-ribonucleotides from RNA. According to this disclosure, rapidly proliferating, substantially noncomminuted seed parts are heated in water to from about 70° to 85° C. for several minutes. Malted barley rootlets are included in the list of seed parts used. The crude mixture of solid and liquid is used to hydrolyze RNA.

In U.S. Pat. No. 3,459,637, ground rootlets or sprouts are extracted with water and the filtered extracts are used to hydrolyze RNA. In order to obtain 5'-nucleotides from RNA using this crude extract, it is necessary to carry out the reaction with RNA at a high pH, between 8.5 and 9.5. Zinc ions are added to accelerate the reaction.

U.S. Pat. No. 3,516,907 discloses a method for obtaining 5'-nucleotides by reacting nucleic acids with a 5'-phosphodiesterase active extract. This extract is obtained by extracting plant material, such as barley sprouts, with water. The crude extract could be further purified by gel fractionation or selective precipitation with a solvent. Heat treatment of the vegetable extract, preferably in the presence of a heavy metal salt, is also disclosed.

A method for producing a yeast extract of improved flavor is disclosed in U.S. Pat. No. 4,303,680. The method involves treating yeast RNA with a crude 5'-phosphodiesterase enzyme solution. The enzyme solution is obtained by extracting broken malt roots with water and then heating the clear filtrate at a temperature of 60° to 65° C. for 5 to 10 minutes.

Although the foregoing references disclose general methods for extracting an enzyme solution having phosphodiesterase activity from plant parts, the general methods are only suitable for use on a laboratory scale. Furthermore, these crude extracts tend to lose activity on storage unless they are kept in a frozen state.

We have now discovered a process for producing a 5'-phosphodiesterase enzyme preparation with low 5'-nucleotidase content which is adaptable to large-scale commercial production. This process is capable of producing both liquid and solid enzyme preparations which have excellent storage stability.

The present process is based on two discoveries. The tightly bound to ground barley malt sprouts than is the desired 5'-phosphodiesterase. The second discovery is that when aqueous slurries of the ground sprouts are heated, the ratio of 5'-phosphodiesterase to 5'-nucleotidase increases more rapidly if the solid material is first removed from the slurry.

SUMMARY OF THE INVENTION

Briefly, in accordance with this invention, there is provided a process for producing a 5'-phosphodiesterase enzyme preparation from barley malt sprouts which comprises:

mixing ground barley malt sprouts with water to give a first aqueous slurry of ground barley malt sprouts;

separating the larger particles of ground barley malt sprouts from said first aqueous slurry in a first separation step to give a second aqueous slurry containing finely-divided barley malt sprouts;

then separating the finely-divided barley malt sprouts from said second aqueous slurry in a second separation step to give a clarified aqueous enzyme extract having less than about 1% by weight of water-insoluble solids;

concentrating the clarified aqueous enzyme extracted by ultrafiltration to give a concentrated enzyme extract; and heating the concentrated enzyme extract at a pH between about 4.3 and about 5.4 at a temperature of between about 60° C. and about 65° C. for from about 15 to about 60 minutes to give an enzyme preparation having a ratio of 5'-phosphodiesterase units to 5'-nucleotidase units of at least about 7:1.

DETAILED DESCRIPTION OF THE INVENTION

The process of this invention is applicable to any plant parts which contain appreciable quantities of 5'-phosphodiesterase enzyme. Rapidly proliferating parts of germinating seeds, such as rootlets and stems, are a particularly rich source of this enzyme. Particularly suitable are the rootlets of seeds which can be malted, such as oats, barley, wheat, corn, rye, mullet, sorghums and rice. Since barley is commonly germinated in large quantities for the production of malt, barley malt sprouts are generally available as a by-product of the malting process. These sprouts are a preferred raw material for the present process.

More 5'-phosphodiesterase can be extracted from the plant material if the material is first broken by a grinding operation. This can be accomplished by any conventional means for reducing the size of particles, such as a hammer mill or other conventional mill. The practice of this invention, it is convenient to provide ground particles of such a size that they will pass through a screen having 1.65 mm openings.

In the process of this invention, the ground plant material is mixed with water to extract the water-soluble enzyme. For convenience in mixing, it is preferred to use at least about 8 parts by weight of water per part of plant material. Under preferred conditions, the pH of the mixture is between about 4.0 and 5.0, the temperature of the mixture is maintained between about 12° C. and about 20° C. Although the time of extraction is not critical, sufficient time should be given for good contact between the water and the solid material.

It has been discovered that the process is more satisfactory if a preservative is added to the water used for the enzyme extraction. Commonly-used food preservatives, such as sodium benzoate and methyl p-hydroxybenzoate are suitable for this process. A combination of these two preservatives is particularly effective.

As noted above, the success of the present process depends on the removal of much of the insoluble material from the extract before the extract is heated.

It has been discovered that this process removes a considerable portion of the undesired 5'-nucleotidase which is bound more tightly to the solid sprout material than is the 5'-phosphodiesterase. A further unexpected finding is that the ratio of 5'-phosphodiesterase to 5'-nucleotidase increases more rapidly on heating if the enzyme extract contains little of the solid sprout material.

Removal of insoluble material from the extract is carried out on a commercial scale by a two-step process. In the first separation step, the larger particles of plant material are separated from the slurry. This step can be carried out by means of various separation devices, such as a belt press, a rotary drum concentrator, or a centrifugal paddle screen. A particularly suitable apparatus for this purpose is the centrifugal paddle screen, ICM Model No. 77, obtained from the Indiana Canning Machine Company, Indianapolis, Indiana, or equivalent, preferably having a screen opening of at least about 50 microns. The filtrate from this first separation step is an aqueous slurry which still contains finely-divided ground plant material in suspension.

The slurry containing the finely-divided material is clarified in a second separation step. Any filtration means which provides rapid separation of finely-divided solids from a liquid may be used. A rotary pre-coat filter, i.e., a vacuum filter coated with a filter aid is particularly suitable for use in this step.

The clarified aqueous enzyme extract obtained from the second separation step is next subjected to concentration by means of ultrafiltration and to heat treatment. Although the order in which the ultrafiltration and heat treatment steps are carried out is not critical, it is more convenient and more economical to concentrate the solution by ultrafiltration before the heat treatment step. Ultrafiltration is carried out by multiple passes of the material through an ultrafiltration apparatus having a membrane which retains material with a molecular weight greater than about 5000 daltons. The ultra-filtration process is carried out until the desired enzyme concentration is obtained. A product with an enzyme concentration of between about 10 times and about 40 times that of the clarified aqueous enzyme extract is usually satisfactory.

The concentrated enzyme extract is then heated at a temperature of between about 60° C. and about 65° C. for about 15 to 60 minutes. The pH of the solution is adjusted to between about 4.3 and about 5.4 before the heat treatment. If a preservative has not been added earlier in the process, it may be added to the concentrated solution before the heat treatment step.

Heating of the concentrated enzyme extract may be carried out as a continuous process. This is accomplished conveniently by passing the extract through a continuous heat exchanger with a rate of flow being adjusted to give the desired heating time. The heated extract is then cooled rapidly to a temperature below about 25° C. to terminate the heating step.

The 5'-phosphodiesterase obtained by the foregoing process has a ratio of 5'-phosphodiesterase units to 5'-nucleotidase units of at least about 7:1, and preferably of at least about 15:1.

It is often desirable to have a solid 5'-phosphodiesterase enzyme preparation. This can be prepared by removing the water from the concentrated enzyme extract under reduced pressure. This is conveniently carried out by a freeze-drying operation using a lyophilizer. The solid enzyme preparation obtained by this process has a concentration of 5'-phosphodiesterase of at least about 800 units per gram of solid.

5'-phosphodiesterase activity units are determined as follows: The substrate is a 10 mM solution of bis-(p-nitrophenyl) phosphate (NPP). A solution of 0.1 ml of the enzyme diluted to a concentration of 0.2 to 2.0 units/ml and 0.1 ml of tris/acetate buffer, pH 6.0, and 0.7 ml of water is incubated at 60° C. for 1 minute. Then 0.1 ml of NPP solution is added. The reaction is stopped after 10 minutes by the addition of 0.3 ml of sodium carbonate solution. The absorbance at 420 nm is determined. A blank is run in which no enzyme is added to the solutions. The absorbance of the blank is subtracted from the absorbance of the enzyme solution. A phosphodiesterase unit is defined as the amount of enzyme that will produce an absorbance of 1.0 in 1 minute at 60° C., pH 6.0.

5'-nucleotidase activity is determined as follows: The reagent is 5'-guanosine monophosphate. A solution of 0.05 ml of enzyme solution (diluted 1 to 10 in water), 0.05 ml tris/acetate buffer, pH 6.0, and 0.35 ml water is incubated at 60° C. for 1 minute. Then 0.05 ml of 100 mM 5'-guanosine monophosphate is added. After 10 minutes, 0.5 ml of 12% trichloroacetic acid is added. After an additional 10 minutes, the amount of inorganic phosphate is determined using the microcolorimetric method of Taussay and Shorr, *J. Biol. Chem.*, 202, 675–685 (1953). A blank is run to determine the amount of inorganic phosphate present in the enzyme that will release 1 umole of phosphate per minute at 60° C., pH 6.0.

The 5'-phosphodiesterase enzyme preparation obtained by the process of this invention is an excellent catalyst for the preparation of 5'-nucleotides from RNA. The enzyme preparation is also useful in applications where it is desirable to hydrolyze or remove nucleic acids. For example, it may be used to improve the filterability of a microbial broth. In addition, the enzyme preparation of this invention may be used to treat microbial broths before they are passed over ion-exchange resins. Such treatment greatly reduces the tendency of the microbial broths to foul the resins.

The following examples serve to illustrate the present invention. All parts and percentages are by weight unless otherwise specified.

EXAMPLE 1

An aqueous slurry of ground barley malt sprouts was passed through a continuous centrifuge. The overflow from the centrifuge, which contained 4% insoluble solids in suspension, was then filtered through a precoated filter. The filtrate, which contained 2.5% insoluble solids in suspension, was further separated in a high-speed centrifuge to give a clarified, solidsfree, liquid. Samples of the three fractions, which contained 4%, 2.5% and 0% insoluble solids, respectively, were analyzed before and after heating at 60° C. for various times. The results given in the table show that the 5'-nucleotidase is bound more tightly to the solids. As a consequence, the ratio of 5'-phosphodiesterase to 5'-nucleosidase is increased by removal of solids from the extracts. The test results also demonstrate that samples with higher solids content respond less well to heat treatment at 60° C. Their 5'-phosphodiesterase content is lost more rapidly when they are heated, and their ratio of 5'-phosphodiesterase to 5'-nucleotidase does not increase nearly as rapidly as do the ratios of extracts with lower solids content.

TABLE

Effect of Heating at 60° C. on 5'-Phosphodiesterase(P) and 5'-Nucleotidase(N) Content of Barley Malt Sprout Extracts Activities in Units/ml

| Time | 4% Solids | | | 2.5% Solids | | | 0% Solids | | |
|---|---|---|---|---|---|---|---|---|---|
| (min) | P | N | P/N | P | N | P/N | P | N | P/N |
| 0 | 20.7 | 4.11 | 5.0 | 16.5 | 3.16 | 5.2 | 13.1 | 0.84 | 15.6 |
| 10 | 16.5 | 2.63 | 6.3 | 13.7 | 1.47 | 9.3 | 11.2 | 0.63 | 17.8 |
| 20 | 13.9 | 1.58 | 8.8 | 12.6 | 0.84 | 15.0 | 11.0 | 0.42 | 26.2 |
| 30 | 9.5 | 0.95 | 10.0 | 9.9 | 0.63 | 15.7 | 10.6 | 0.42 | 25.2 |

EXAMPLE 2

Barley malt sprouts were ground and passed through a screen having a sieve opening of 1.65 mm. To a mixture of 1 part of the ground sprouts and 10 parts by weight of water was added 4.8 g of sodium benzoate and 0.9 g of methyl p-hydroxybenzoate per liter of slurry. Sufficient citric acid solution was added to adjust the pH to 4.6±0.1. The slurry was agitated for 30 minutes. Then the larger solid particles were removed by passing the slurry through a paddle screen apparatus, ICM No. 77, having a screen opening of about 50 microns manufactured by the Indiana Canning Machine Company. The effluent from the paddle screen, which contained finely-divided solids in suspension, was clarified by passing through a rotary vacuum filter coated with a diatomaceouis earth filter aid (CELATOM FW40, available from Eagle-Picher Industries, Inc., Cincinnati, Ohio) with spray water washing. The clarified aqueous enzyme extract was concentrated by means of an ultrafiltration unit having a membrane which retains material having a molecular weight of about 5000 daltons. The solution was concentrated until the enzyme concentration was approximately 30 times that of the clarified aqueous enzyme extract. The concentrate from the ultrafiltration unit was then heated at 63°±1° C. for 15 minutes by passing it through a heated holding coil. It was then cooled quickly to about 21° C. From 6193 kg of barley malt sprouts there was obtained 802.5 kg of extract containing 120 units/g of 5'-phosphodiesterase units to 5'-nucleotidase units in this extract was 52:1.

EXAMPLE 3

The general procedure of Example 2 was repeated except that the first separation step was carried out by means of an Eimco belt press, available from the Process Equipment Company, Palatine, Illinois. The concentrated enzyme preparation contained 73 units/g of 5'-phosphodiesterase enzyme and 1.1 units/g of 5'-nucleotidase units.

A 15.89 kg portion of the enzyme concentrate was freeze-dried using a commercial lyophilizer. The yield of light-brown solid containing 855 units/g of 5,-phosphodiesterase enzyme was 1.21 kg. The ratio of 5'-phosphodiesterase units to 5'-nucleotidase units in this product was about 50:1. The product is stable when stored at room temperature.

Thus, there has been provided, in accordance with this invention, a 5'-phosphodiesterase enzyme preparation and process for its production. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for producing a 5'-phosphodiesterase enzyme preparation from barley malt sprouts which consists essentially of the steps mixing ground barley malt sprouts with water to give a first aqueous slurry of ground barley malt sprouts;

separating the larger particles of ground barley malt sprouts from said first aqueous slurry in a first separation step to give a second aqueous slurry containing finely-divided barley malt sprouts;

then separating the finely-divided barley malt sprouts from said second aqueous slurry in a second separation step to give a clarified aqueous enzyme extract having less than about 1% by weight of water-insoluble solids;

concentrating the clarified aqueous enzyme extract by ultrafiltration to give a concentrated enzyme extract; and heating the concentrated enzyme extract at a pH between about 4.3 and about 5.4 at a temperature of between about 60° C. and about 65° C. for from about 15 to about 60 minutes to give an enzyme preparation having a ratio of 5'-phosphodiesterase units to 5'-nucleotidase units of at least about 7:1.

2. The process of claim 1 wherein the barley malt sprouts are ground to pass through a screen having a sieve opening of 1.65 mm.

3. The process of claim 2 wherein the ground barley malt sprouts are mixed with at least 8 parts by weight of water per 1 part by weight of barley malt sprouts.

4. The process of claim 3 wherein the ground barley malt sprouts are mixed with water at a pH between about 4.0 and about 5.0 and at a temperature between about 12° C. and about 20° C.

5. The process of claim 4 wherein a preservative is added to the water mixed with the ground barley malt sprouts.

6. The process of claim 5 wherein the preservative is selected from the group: sodium benzoate, methyl p-hydroxybenzoate, and mixtures thereof.

7. The process of claim 1 wherein the first separation step is carried out by means of a paddle screen.

8. The process of claim 1 wherein the second separation step is carried out by means of a rotary precoat filter.

9. The process of claim 1 wherein the ultrafiltration is carried out by means of ultrafiltration equipment having a membrane which retains material having a molecular weight greater than about 5000 daltons.

10. The process of claim 1 wherein the concentrated enzyme extract is heated in a continuous process by passing through a heat exchanger and then cooled rapidly.

11. The process of claim 10 wherein the heated enzyme extract is cooled to a temperature below about 25° C.

12. The process of claim 1 wherein the enzyme preparation has a ratio of 5'-phosphodiesterase units to 5'-nucleotidase units of at least about 15:1.

13. A 5'-phosphodiesterase enzyme preparation prepared by the process of claim 5.

14. A 5'-phosphodiesterase enzyme preparation of claim 13 wherein the preparation is freeze-dried to give a solid enzyme preparation.

15. A 5'-phosphodiesterase enzyme preparation of claim 14 wherein the concentration of 5'-phosphodiesterase is at least 800 units per gram of solid.

* * * * *